United States Patent [19]
Aven

[11] Patent Number: 6,165,940
[45] Date of Patent: Dec. 26, 2000

[54] NON-AQUEOUS SUSPENSION CONCENTRATE

[75] Inventor: Michael Aven, Mainz, Germany

[73] Assignee: American Cyanamid Co., Madison, N.J.

[21] Appl. No.: 09/382,092

[22] Filed: Aug. 24, 1999

Related U.S. Application Data

[60] Provisional application No. 60/101,704, Sep. 25, 1998.

[51] Int. Cl.[7] ................................................. A01N 63/00
[52] U.S. Cl. .............................................. 504/118
[58] Field of Search ...................... 504/116, 118

[56] References Cited

U.S. PATENT DOCUMENTS 5,817,663  10/1998  Pees et al. ............................. 544/263

FOREIGN PATENT DOCUMENTS

| | | |
|---|---|---|
| 0 071 792 A2 | 2/1983 | European Pat. Off. ...... C07D 487/04 |
| 0 103 171 A1 | 3/1984 | European Pat. Off. ....... A01N 25/04 |
| 0 149 459 A2 | 8/1985 | European Pat. Off. ....... A01N 25/04 |
| 0 313 317 B1 | 4/1989 | European Pat. Off. ....... A01N 47/36 |
| 0 456 198 A1 | 11/1991 | European Pat. Off. ....... A01N 37/40 |
| 0 645 083 A1 | 3/1995 | European Pat. Off. ....... A01N 43/50 |
| 0 789 999 A2 | 8/1997 | European Pat. Off. ....... A01N 25/30 |
| 0 943 241 A1 | 9/1999 | European Pat. Off. ....... A01N 43/90 |
| 2 083 360 | 3/1982 | United Kingdom ........... A01N 47/34 |

*Primary Examiner*—S. Mark Clardy
*Assistant Examiner*—Alton Pryor
*Attorney, Agent, or Firm*—Joseph M. Mazzarese; Barbara V. Maurer

[57] ABSTRACT

The invention relates to a non-aqueous, stable suspension concentrate which comprises (a) 50 to 400 g/L of one or more crop protection active compounds, (b) 50 to 700 g/L of one or more adjuvants, (c) 75 to 500 g/L of one or more organic solvents, at least one dispersant selected from the groups (d) and (e)

(d) 5 to 150 g/L of one or more non-ionic dispersants, (e) up to 150 g/L of one or more anionic dispersants, and optionally (f) up to 100 g/L of one or more thickeners, and to the pesticidal use of such a suspension.

14 Claims, No Drawings

NON-AQUEOUS SUSPENSION CONCENTRATE

This application claims priority from copending provisional application(s) Ser. No. 60/101704 filed on Sep. 25, 1998

BACKGROUND OF THE INVENTION

This invention concerns a non-aqueous, stable suspension concentrate (SC) for crop protection active compounds, a method for the manufacture of such suspensions, and their use for combating pests.

As a rule, inert ingredients must be used to provide crop protection active compounds, for example fungicidal compounds, in a form that the user can apply, either as such or after dilution with water. The right choice of suitable inert ingredients, such as carriers, for the formulation often determines to a significant extent whether the active ingredient exhibits its full efficacy on application. Not every active ingredient is suitable for use in any given formulation, because both the efficacy and physiochemical stability of the active ingredient may be affected by other ingredients in the formulation.

The efficacy of the active components can often be improved by addition of other ingredients. The observed efficacy of the combination of ingredients can sometimes be significantly higher than that would be expected from the amounts of the individual ingredients used (synergism). An adjuvant is defined here as a substance which can increase the biological activity of an active ingredient but is not itself significantly biologically active. The adjuvant can either be included in the formulation or can be added separately, e.g., to a spray tank together with the formulation containing the active ingredient.

For easy and safe handling and dosing of these adjuvants by the end-user, and to avoid unnecessary packing material, it is desirable to develop concentrated formulations which already contain such adjuvants.

The International Patent Application WO 95/01722 discloses aqueous pesticidal formulations containing non-ionic dispersants selected from block-polymers having a polyoxypropylene core, an anionic dispersant, and a wetting agents selected from polyalkoxylated fatty alcohols. However, it is not stated that these wetting agents enhance the activity of the pesticides. Moreover, there is no disclosure of non-aqueous suspension concentrates.

SUMMARY OF THE INVENTION

The present invention relates to a non-aqueous, stable suspension concentrate (SC) which comprises
(a) 50 to 400 g/L of one or more crop protection active compounds;
(b) 50 to 700 g/L of one or more adjuvants;
(c) 75 to 500 g/L of one or more organic solvents;
at least one dispersant selected from the groups (d) and (e)
(d) 5 to 150 g/L of one or more non-ionic dispersants,
(e) 5 to 150 g/L of one or more anionic dispersants; and optionally up to 100 g/L of one or more thickeners.

Another aspect of the present invention is a process for the preparation of the SC described above, which comprises:
(a) air-milling component (a) optionally in the presence of component (e), and/or a milling aid such as kaolin or silica; and
(b) mixing all the components (a) to (c), (d) and/or (e) and, optionally, (f) in a dissolver.

Furthermore, the invention relates to a method for the control of pests at a locus which comprises diluting a SC according to the invention with water and treating the locus with an effective amount of the diluted formulation.

DETAILED DESCRIPTION OF THE PREFERRED EMBODIMENTS

It has now been found that, surprisingly, a stable non-aqueous SC comprising one or more crop protection active compounds (a) and one or more adjuvants (b) in combination with one or more organic solvents (c), one or more non-ionic dispersants (d) and/or one or more anionic dispersants (e) and optionally one or more thickeners (f) can be prepared.

It has also surprisingly been found that the biological activity of the active ingredients (a) can be increased by including the adjuvants (b) in the spray dilution or directly in the formulation. In the formulation of the present invention, the adjuvants (b) are incorporated into the concentrated formulation.

The term pests as used herein includes, but is not limited to, plant pathogens, insects and weeds.

In principle, all crop protection active compounds can be used in non-aqueous concentrated suspensions according to the invention. Solid crop protection active compounds are preferred.

Preferably, the solid crop protection active compounds are less than moderately soluble in the organic solvent (c). A solubility of less than 10 g/L, in particular less than 5 g/L, in solvent (c) is preferred.

The compositions of this invention can be applied to the plants or their environment with additional active substances, such as fertilizers, or agents containing trace elements, or other preparations which influence plant growth, or selective herbicides, insecticides, fungicides, bactericides, nematicides, algicides, molluscicides, rodenticides, virucides, compounds inducing resistance in plants, biological control agents, such as viruses, bacteria, nematodes, fungi and other microorganisms, repellents of birds and animals, and plant growth regulators, or mixtures of several of these substances.

The active ingredients provided in the form of the non-aqueous SC formulation according to the invention include all suitable biologically active compounds for plant protection, preferably fungicides, herbicides, insecticides, acaricides, nematicides and repellents, in particular fungicides. Active ingredients which are solid at room temperature are preferred, in particular those with a melting point higher than 50 ° C.

Mixtures of different biologically active compounds can have a broader spectrum of activity than a single compound alone. Furthermore, these can exhibit a synergistic effect. In a preferred embodiment, the formulation of the present invention contains a mixture of active ingredients, wherein one of the active ingredients may be dissolved in the continuous phase of the SC formulation according to the invention.

Preferred fungicides for use in the compositions of the present invention are the commercially available compounds selected from the group consisting of:

anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, iprovalicarb, kasugamycin, kitazin P, kresoxim-methyl, mancozeb, maneb, mepanipyrim, mepronit, metalaxyl, metconazole, methfuroxam, MON 65500, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanatemethyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, and ziram.

In addition, the formulations according to the invention may contain at least one compound of the following classes of biological control agents: viruses, bacteria, nematodes, fungi, and other microorganisms which are suitable for the control of insects, weeds or plant diseases, or to induce host resistance in the plants. Examples of such biological control agents are: *Bacillus thuringiensis, Verticillium lecanii, Autographica californica* NPV, *Beauvaria bassiana, Ampelomyces quisqualis, Bacilis subtilis, Pseudomonas fluorescens, Steptomyces griseoviridis* and *Trichoderma harzianum*.

Moreover, the formulations according to the invention may contain at least one chemical agent that induces the systemic acquired resistance in plants such as, for example, nicotinic acid or derivatives thereof, 2,2-dichloro-3,3-dimethylcylopropylcarboxylic acid, or BION.

Also preferred are compositions that include derivatives of triazolopyrimidines which are disclosed, for example, by European Patent Applications EP 0 071 792 and EP-A-0 550 113, in particular the compounds of formula I

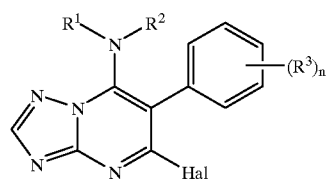

(I)

in which
R¹ and R² each independently represent hydrogen or an optionally substituted alkyl, alkenyl, alkynyl, alkadienyl, haloalkyl, aryl, heteroaryl, cycloalkyl, bicycloalkyl or heterocyclyl group, or R¹ and R² together with the adjacent nitrogen atom represent an optionally substituted heterocyclic ring, R³ represents a halogen atom or an alkyl or alkoxy group, n represents an integer from 0 to 5, and Hal represents a halogen atom.

More preferred are those compounds of formula I wherein R¹ and R² together with the interjacent nitrogen atom represent an optionally substituted 6-membered heterocyclic ring, in particular a 4-methylpiperid-1-yl group; or R¹ represents a $C_{1-6}$ alkyl, a $C_{1-6}$ haloalkyl, in particular a $C_{2-6}$ fluoroalkyl, or a $C_{3-8}$ cycloalkyl group and R² represents a hydrogen atom or a $C_{1-6}$ alkyl group and/or wherein

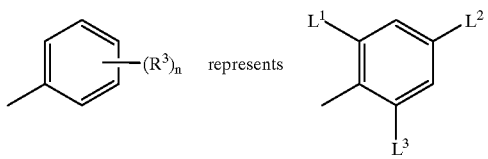

in which L¹ represents a halogen atom, preferably fluorine or chlorine and

L² and L³ each independently represent a hydrogen atom or a halogen atom, preferably fluorine; and/or wherein Hal represents a chlorine atom.

Most preferred are those compounds of formula I wherein R¹ represents a $C_{2-5}$ fluoroalkyl group, in particular a 2,2,2-trifluoroethyl or 1,1,1-trifluoroprop-2-yl group; and R² represents a hydrogen atom.

Another group of preferred fungicidal compounds are the benzoylbenzenes which are disclosed, for example, by European Patent Application EP-A-0 727 141.

Preferred herbicides include the commercially available compounds selected from the group consisting of:
2,4-D, 2,4-DB, 2,4-DP, acetochlor, acifluorfen, alachlor, alloxydim, ametrydione, amidosulfuron, asulam, atrazin, azimsulfuron, benfuresate, bensulfuron, bentazon, bifenox, bromobutide, bromoxynil, butachlor, cafenstrole, carfentrazone, chloridazon, chlorimuron, chlorpropham, chlorsulfuron, chlortoluron, cinmethylin, cinosulfuron, clomazone, clopyralid, cyanazin, cycloate, cyclosulfamuron, cycloxydim, daimuron, desmedipham, di-methazone, dicamba, dichlobenil, diclofop, diflufenican, dimethenamid, dithiopyr, diuron, eptame, esprocarb, ethiozin, fenoxaprop, flamprop-M-isopropyl, flamprop-M-methyl fluazifop, fluometuron, fluoroglycofen, fluridone, fluroxypyr, flurtamone, fluthiamid, fomesafen, glufosinate, glyphosate, halosafen, haloxyfop, hexazinone, imazamethabenz, imazamethapyr, imazamox, imazapyr, imazaquin, imazethapyr, ioxynil, isoproturon, isoxaben, isoxaflutole, lactofen, MCPA, MCPP, mefenacet, metabenzthiazuron, metamitron, metazachlor, methyldimron, metolachlor, metribuzin, metsulfuron, molinate, nicosulfuron, norflurazon, oryzalin, oxadiargyl, oxasulfuron, oxyfluorfen, pendimethalin, picloram, pretilachlor, propachlor, propanil, prosulfocarb, pyrazosulfuron, pyridate, qinmerac, quinchlorac, quizalofopethyl, sethoxydim, simetryne, sulcotrione, sulfentrazone, sulfosate, terbutryne, terbutylazin, thiameturon, thifensulfuron, thiobencarb, tralkoxydim, triallate, triasulfuron, tribenuron, triclopyr, trifluralin.

Furthermore preferred are the derivatives of aryloxypicolineamides which are disclosed, for example, by European Patent Application EP-A-0 447 004, in particular, N-(4- fluorophenyl) 6-(3-trifluoromethylphenoxy)-pyrid-2-ylcarboxamide having the proposed common name picolinafen.

Examples of insecticidal compounds are alpha-cypermethrin, benfuracarb, BPMC, buprofezine, carbosulfan, cartap, chlorfenvinphos, chlorpyrifos-methyl, cycloprothrin, cypermethrin, esfenvalerate, ethofenprox, fenpropathrin, flucythrinate, flufenoxuron, hydramethyinon, imidacloprid, isoxathion, MEP, MPP, nitenpyram, PAP, permethrin, propaphos, pymetrozine, silafluofen, tebufenozide, teflubenzuron, temephos, terbufos, tetrachlorvinphos and triazamate.

The non-aqueous SC according to the invention comprises 50 to 400 g/L, preferably 75 to 250 g/L, more preferably 80 to 200 g/L of one or more crop protection active compounds.

The adjuvants (b) are preferably liquid polyalkoxylated aliphatic alcohols or amines. These adjuvants may be obtained by alkoxylation of fatty alcohols or amines having 9–24, preferably 12–22 and in particular 14–20 C-atoms, with alkyleneoxide having 2–6, preferably 2–3 C-atoms, in particular with a mixture of ethylenoxide and propyleneoxide. The aliphatic moieties of the said fatty alcohols and amines may be straight-chained or branched. Preferably these compounds correspond to mixed random or block oligomers of the following formula

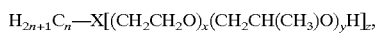

in which

X represents O or N, z is 1, in the event that X represents O, or 2 in the event that X represents N, and the average of the indexes given is as follows:

n is an integer from 9 to 20, in particular 15 to 19;

x is an integer from 1 to 8, in particular 2 to 6; and y is an integer from 6 to 12, in particular 7 to 10.

Particularly preferred in the practice of this invention are those polyalkoxylated aliphatic alcohols or amines which are liquids at temperatures down to at least 20° C. and have a viscosity of 30 to 100, in particular 50 to 80 mPa·s at 25°C. The compounds which are commercially available under the trademark Plurafac® LF (Tensid-Chemie, Köln/BASF AG, Ludwigshafen) and certain ATPLUS®-types (ICI Surfactants, Eversberg), in particular Plurafac® LF 224, Plurafac® LF 403, Plurafac® LF 700 and Plurafac® LF 1300, ATPLUS® 245 or SCS4774 (ICI Surfactants) have been proven to be especially advantageous.

In another preferred embodiment of the present invention, the adjuvant (b) is preferably a polyoxyalkylene triglyceride. These adjuvants are obtainable by alkoxylation of triglycerides, resulting in mixtures of compounds with one to three glyceride side chains having 9–24, preferably 12–22 and in particular 14–20 C-atoms, in particular with ethyleneoxide. The aliphatic moieties of the triglycerides may be straight-chained or branched. Preferably, these compounds are mixed oligomers resulting from the alkoxylation of castor or canola oil.

A particularly preferred adjuvant (b) is castor oil ethoxylate, for example Ukanil® 2507, which is commercially available from ICI Surfactants, or canola oil alkoxylate, for example EMULGIN CO3522, which is commercially available from Henkel KGaA.

The non-aqueous SC of this invention comprises 50 to 700 g/L, preferably 200 to 600 g/L, more preferably 300 to 500 g/L of one or more adjuvants.

In a particularly preferred embodiment of the present invention, the adjuvant (b) comprises two or more different alkoxylated derivatives, one of which is an alkoxylated triglyceride, in particular an ethoxylated triglyceride. The non-aqueous SC of this invention preferably comprises 5 to 150 g/L, more preferably 20 to 100 g/L, in particular 40 to 75 g/L of one or more alkoxylated triglyceride, and 45 to 550 g/L of one or more alkoxylated alcohol or amine.

The efficacy of the fungicidal triazolopyrimidines of formula I can be enhanced by addition of adjuvants (b).

In a particularly preferred embodiment, the triazolopyrimidine of formula I is 5-chloro-6-(2-chloro-6-fluorophenyl)-7-(2,2,2-trifluoroethylamino)-[1,2,4]triazolo[1,5-a]pyrimidine (Compound IA), or 5-chloro-6-(2,4,6-trifluorophenyl)-7-(1,1,1-trifluoroprop-1-ylamino)-[1,2,4]triazolo[1,5-a]pyrimidine (Compound IB).

The appropriate relative amounts of active ingredient (a) and the adjuvant (b) lie, in accordance with the invention, between 1:1 and 1:100, preferably between 1:1 and 1:10 and, in particular, between 1:2 and 1:5. Generally, the pesticidal efficacy can be enhanced to a higher degree by the addition of larger amounts of the adjuvant (b), as is shown in the experimental results described below.

Recommended doses for various applications are known for the plant protection active compounds (a); however, the efficacy can be enhanced in accordance with the invention. Addition of the adjuvants of this invention can (depending on the active ingredient, the adjuvant and their amounts) reduce the amount of active ingredient needed per hectare by half or more, making it possible to control additional diseases at reasonable doses.

An important advantage of the invention is the rapid onset and the high persistency of activity. This enlarges the period for application of the pesticide and makes its use more flexible.

The pesticidal formulations according to the present invention can be used protectively and curatively.

The solvent (c) is suitably a water immiscible solvent in which the solubility of the crop protection compound (a) is less than 5 g/L. Preferably, it is an apolar organic solvent selected from the group consisting of aromatic hydrocarbons, aliphatic hydrocarbons, alkyl lactates, glycols and plant oil esters or mixtures thereof. Preferred aromatic hydrocarbons are e.g. toulene, xylenes, or substituted naphthalenes as for example Solvesso® 200(Deutsche Exxon Chemicals) or Shellsol® A (Deutsche Shell AG), preferred aliphatic hydrocarbons are e.g. cyclohexane, paraffins as for example Isopar® H (Deutsche Exxon Chemicals) or Shellsol® T (Deutsche Shell AG), preferred plant oil esters are methylated coconut or soybean oil esters, in particular methyl caprylate such as Witconol 1095 (Witco Corp.), preferred alkyl lactates are ethyl and 2-ethylhexyl lactate, preferred glycols are dialkyl diethyleneglycols, in particular diethyl diethyleneglycol. Mixtures of different solvents are often suitable.

The non-aqueous SC according to the invention comprises 75 to 500 g/L, preferably 100 to 450 g/L, in particular 200 to 420 g/L of one or more organic solvents.

The non-ionic dispersant (d) is preferably an ethoxylated non-ionic dispersant different from the adjuvants (b), more preferably polyethyleneoxide-polypropyleneoxide block-copolymers, for example PLURONIC®-type block-copolymers, which are available from BASF AG, or polyoxyethylene fatty acid or polyoxyethylene alcohols. These disperants are obtainable by alkoxylation of fatty acids, alcohols or alkylphenols having 9–24, preferably 12–22 and in particular 14–20 C-atoms, with ethyleneoxide. The aliphatic moieties of the fatty alcohols may be straight-chained or branched. Preferred dipersants (d) include ARKOPAL®- type alkyl- and/or alkylarylethoxylates (Clariant GmbH former Hoechst AG) or GENAPOL®-type(Clariant GmbH former Hoechst AG) alkanoylethoxylates.

The non-aqueous SC according to the invention preferably comprises 5 to 150 g/L, more preferably 20 to 100 g/L, in particular 40 to 75 g/L of one or more non-ionic dispersants. In a preferred embodiment of the present invention, the SC formulation is essentially free of non-ionic dispersants (d).

The anionic dispersant (e) is suitably an alkali or alkaline earth metal sulfonate, including highly concentrated mixtures of such a sulfonate with a polar diluent, such as an alcohol, or an aromatic hydrocarbon, preferably butanol or Solvesso®200. Such a mixture preferably consists of 40 to 90 wt % of at least one alkali or alkaline earth metal sulfonate and 10 to 60 wt % of a polar diluent. Alkaline earth metal alkylbenzene sulfonates are preferred, in particular calcium dodecylbenzene sulfonate (such as Rhodocal® 70/B (Rhodia former Rhone Poulenc)) or tetrapropylene benzene sulfonates (such as PHENYLSULFONAT CA100 (Clariant GmbH)).

The non-aqueous SC according to the invention preferably comprises 5 to 150 g/L, more preferably 20 to 100 g/L, in particular 30 to 70 g/L of one or more anionic dispersants.

The thickener (f) is preferably an organo clay or a hydrated silicate, especially a hydrated aluminium magnesium silicate such as Attagel® 50 (Engelhard Corp.) or bentonite derivatives such as BENTONE® SD-1 or SD-3 (Rheox, Inc. Hightstown, N.J., USA)., pyrogenic silicic acid such as Car-O-Sil M5 (Cabot GmbH, Rheinfelden, Germany), polyamides or polesters such as THIXATROL® Plus or THIXATROL® 289 (Rheox, Inc. Hightstown, N.J., USA).

The non-aqueous SC according to the invention may comprise up to 100 g/L, preferably 10 to 100 g/L, in particular 30 to 75 g/L of one or more thickeners.

In a particularly preferred embodiment according to this invention the non-aqueous SC essentially consists of (a) 75 to 250 g/L of one or more crop protection active compounds, in particular a compound of formula I;

(b) 200 to 650 g/L of one or more ingredients selected from the group consisting of $C_{9-20}$ alcohols or amines being alkoxylated with 2 to 20 $C_{2-6}$ alkoxy groups, in particular PLURAFAC® LF 700 or ATPLUS® 245, and alkoxylated triglycerides, in particular UKANIL® 2507;

(c) 100 to 450 g/L of one or more organic solvents selected from the group consisting of hydrocarbons, aliphatic hydrocarbons, alkyl lactates, glycols and plant oil esters;

(d) 0 to 50 g/L of a polyoxyethylene fatty acid;

(e) 20 to 100 g/L of an alkali or alkaline earth metal sulfonate, in particular Rhodocal® 70/B or PHENYL-SULFONAT CA100; and (f) 10 to 100 g/L of one or more silicates or organo clays, in particular Attagel® 50.

The ingredients may be processed to form a suspension concentrate according to the invention by well-established techniques, including intensive mixing and/or milling of the active ingredients with the other substances, such as solvents, dispersants, and adjuvants. The desired form of application, such as spraying, atomizing, dispersing or pouring, will depend on the desired objectives and the given circumstances, and can be readily determined by one skilled in the art.

Suspension concentrates according to the present invention are usually produced so as to obtain a stable, non-sedimenting, flowable product containing 5 to 40% w/v active ingredient, 0.5 to 30% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and an organic liquid in which the active ingredient is substantially insoluble.

In a preferred embodiment, the crop protection compound (a) is air-milled before admixing the components (b) to (f).

The finished non-aqueous suspension concentrates according to tile invention are stable in storage, even over a relatively long period. Although phase separation may occur upon storage due to sedimentation of the active ingredient, no aggregates are formed. The SCs according to the present invention may include high loadings of one or more adjuvants in a one-pack formulation with a pesticide and, therefore, offer the advantage of an optimized and easy-to-use formulation of the crop protection active compound. The separate addition of an adjuvant by the end-user before application is, therefore, unnecessary.

Aqueous dispersions and emulsions, for example compositions obtained by diluting the SC of the invention with water, also lie within the scope of the invention.

As a commodity, the compositions preferably may be in a concentrated form, whereas the end user generally employs diluted compositions. The compositions may be diluted to a concentration down to 0.001% of active ingredient. The desired dose usually is in the range from 0.01 to 10 kg a.i./ha.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

Examples of non-aqueous suspension concentrates according to the invention are shown in the following examples A to M:

| Identity of Ingredients used in Examples | |
|---|---|
| Name | Identity |
| Compound IB | Fungicidal Triazolopyrimidine of formula I |
| Rhodocal ® 70/B (Rhodia) | 70% Calcium Dodecylbenzene sulfonate in n-butanol |
| Ukanil ® 2507 (ICI Surfactants) | Castor oil ethoxylate |
| Emulgin ® CO3522 (Henkel) | Canola oil alcoxylate |
| Plurafac ® LF700 (BASF AG) | alcohol alcoxylate |
| SCS4774 (ICI Surfactants) | branched alcohol alcoxylate |
| Witconol ® 1095 (Witco Corp.) | 95% $C_{10}$ methylated plant oil (95% methyl caprylate) |
| Isopar ® H (Exxon) | Isoparaffinic mixture, distillation range 182–192° C. |
| Shellsol ® T (Shell) | Isoparaffinic mixture, $C_{11}$–$C_{13}$ |
| Solvesso ® 200 (Exxon) | Aromatic mixture, distillation range 231–287° C. |
| Attagel ® 50 (Engelhard Corp.) | hydrated aluminium magnesium silicate |

| Example A | | Example B | |
|---|---|---|---|
| Ingredient | amount (g) | Ingredient | amount (g) |
| Compound IB | 100 | Compound IB | 100 |
| Rhodocal 70/B | 50 | Rhodocal 70/B | 50 |

-continued

Identity of Ingredients used in Examples

| | | | |
|---|---|---|---|
| Ukanil 2507 | 50 | Ukanil 2507 | 50 |
| Plurafac LF700 | 480 | Plurafac LF700 | 480 |
| Witconol 1095 | 320 | Isopar H | 320 |

| Example C | | Example D | |
|---|---|---|---|
| Ingredient | amount (g) | Ingredient | amount (g) |
| Compound IB | 100 | Compound IB | 100 |
| Rhodocal 70/B | 50 | Rhododal 70/B | 50 |
| Ukanil 2507 | 50 | Ukanil 2507 | 50 |
| Plurafac LF700 | 400 | Plurafac LF700 | 480 |
| Shellsol T | 400 | Solvesso 200 | 320 |

Physico-chemical Properties

| | Example | | | |
|---|---|---|---|---|
| Property | A | B | C | D |
| Blind formulation | clear | clear | clear | clear |
| Spray dilution of 0.5 ml formulation in graduated cylinder with 100 ml tap water, self-dispersion checked, followed by 30 inversions. | Good | good | good | good |
| Spray dilution 24 h, re-dispersibility of a.i. particles | good | good | good | good |
| Storage of formulation for 2 weeks at 54° C., visual evaluation of particles under microscope | no particle growth | no particle growth | no particle growth | no particle growth |

Example E

| Ingredient | amount (g) |
|---|---|
| Compound IB | 100 |
| Rhodocal 70/B | 50 |
| Ukanil 2507 | 50 |
| Attagel 50 | 60 |
| Plurafac LF700 | 444 |
| Solvesso 200 | to 1 liter |

Physico-chemical Properties

| Property | Example E |
|---|---|
| Density | 1.06 g/ml |
| Flash point | >70° C. |
| Spray dilution of 0.5 ml SC in graduated cylinder with 100 ml tap water, self-dispersion checked. | Good |
| Spray dilution 24 h, redispersibility of a.i. particles | good |

| Example F | | Example G | |
|---|---|---|---|
| Ingredient | amount (g) | Ingredient | amount (g) |
| Compound IB | 100 | Compound IB | 100 |
| Rhodocal 70/B | 50 | Rhodocal 70/B | 50 |
| Ukanil 2507 | 530 | Ukanil 2507 | 50 |
| Attagel 50 | 30 | Attagel 50 | 30 |
| Isopar H | to 1 liter | Plurafac LF700 | 480 |
| | | Isopar H | to 1 liter |

| Example H | | Example I | |
|---|---|---|---|
| Ingredient | amount (g) | Ingredient | amount (g) |
| Compound IB | 100 | Compound IB | 100 |
| Rhodocal 70/B | 50 | Rhodocal 70/B | 50 |
| Ukanil 2507 | 50 | Ukanil 2507 | 50 |

-continued

Identity of Ingredients used in Examples

| | | | |
|---|---|---|---|
| Attagel 50 | 30 | Attagel 50 | 30 |
| SCS4774 | 480 | Emulgin CO3522 | 480 |
| Isopar H | to 1 liter | Isopar H | to 1 liter |

| Example J | | Example K | |
|---|---|---|---|
| Ingredient | amount (g) | Ingredient | amount (g) |
| Compound IB | 100 | Compound IB | 100 |
| Rhodocal 70/B | 50 | Rhodocal 70/B | 50 |
| Ukanil 2507 | 530 | Ukanil 2507 | 530 |
| Attagel 50 | 30 | Attagel 50 | 30 |
| Witconol 1095 | to 1 liter | Ethyl Diglyme | to 1 liter |

| Example L | | Example M | |
|---|---|---|---|
| Ingredient | amount (g) | Ingredient | amount (g) |
| Compound IB | 100 | Compound IB | 100 |
| Rhodocal 70/B | 50 | Rhodocal 70/B | 50 |
| Ukanil 2507 | 530 | Ukanil 2507 | 530 |
| Attagel 50 | 30 | Attagel 50 | 36 |
| Ethyl lactat | to 1 liter | 2-Ethylhexyl lactat | to 1 liter |

What is claimed is:

1. A non-aqueous, stable suspension concentrate (SC) which comprises
   (a) 50 to 400 g/L of one or more crop protection active compounds;
   (b) 200 to 650 g/L of one or more adjuvants;
   (c) 75 to 500 g/L of one or more organic solvents;
   at least one dispersant selected from the groups (d) and (e)
   (d) up to 150 g/L of one or more non-ionic dispersants,
   (e) 5 to 150 g/L of one or more anionic dispersants; and optionally,
   (f) up to 100 g/L of one or more thickeners.

2. A SC in accordance with claim 1 wherein said crop rotection active compounds (a) comprise at least one triazolopyrimidine of formula I

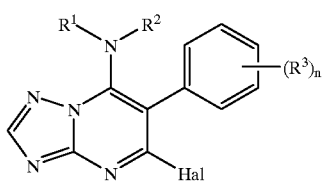

(I)

in which
   $R^1$ and $R^2$ each independently represent hydrogen or an optionally substituted alkyl, alkenyl, alkynyl, alkadienyl, haloalkyl, aryl, heteroaryl, cycloalkyl, bicycloalkyl or heterocyclyl group, or
   $R^1$ and $R^2$ together with the adjacent nitrogen atom represent an optionally substituted heterocyclic ring,
   $R^3$ represents a halogen atom or an alkyl or alkoxy group,
   n represents an integer from 0 to 5, and
   Hal represents a halogen atom.

3. A SC in accordance with claim 1 wherein said adjuvant (b) comprises a compound having 2 to 20 $C_{2-6}$ alkoxy groups.

4. A SC in accordance with claim 3 wherein said adjuvant (b) is a mixed ethoxylate/propoxylate.

5. A SC in accordance with claim 3 wherein said adjuvant (b) is selected from the group consisting of polyalkoxylated alcohols, amines and triglycerides.

6. A SC in accordance with claim 5 wherein said adjuvant (b) comprises two or more different polyalkoxylated derivatives, one of which is a polyalkoxylated triglyceride.

7. A SC in accordance with claim 1 wherein the ratio of said crop protection active compounds (a) to said adjuvant (b) is between 1:100 and 1:1.

8. A SC in accordance with claim 7 wherein said ratio is between 1:10 and 1:1.

9. A SC in accordance with claim 1 wherein the solvent (c) is selected from the group consisting of aromatic hydrocarbons, aliphatic hydrocarbons, alkyl lactates, glycols and plant oil esters, and mixtures thereof.

10. A SC in accordance with claim 1 wherein the non-ionic dispersant (d) is a polyoxyethylene fatty acid.

11. A SC in accordance with claim 1 wherein the anionic dispersant (e) is an alkali or alkaline earth metal sulfonate.

12. A SC in accordance with claim 1 wherein the thickener (f) is an organo clay.

13. A process for the preparation of a SC as claimed in claim 1, which comprises (a) air-milling of 50 to 400 g/L of one or more crop protection active compounds (a) optionally in the presence of one or more anionic dispersant (e), and/or a milling aid, and (b) mixing all the components (a) to (c), (d) and/or (e) and optionally (f) in a dissolver.

14. A method for the control of pests at a locus which comprises diluting a SC as claimed in claim 1 with water and treating the locus with a pesticidally effective amount of the diluted formulation.

* * * * *